(12) United States Patent
Kanev et al.

(10) Patent No.: US 10,048,844 B2
(45) Date of Patent: Aug. 14, 2018

(54) OPERATING METHOD FOR INSPECTING EQUIPMENT

(71) Applicant: MPI Corporation, Chu-pei, Hsinchu County (TW)

(72) Inventors: Stojan Kanev, Chu-pei (TW); Yung-Chin Liu, Chu-pei (TW); Andrej Rumiantsev, Chu-pei (TW); Yao-Chuan Chiang, Chu-pei (TW)

(73) Assignee: MPI CORPORATION, Chu-Pei, Hsinchu County (TW)

( * ) Notice: Subject to any disclaimer, the term of this patent is extended or adjusted under 35 U.S.C. 154(b) by 449 days.

(21) Appl. No.: 14/996,282

(22) Filed: Jan. 15, 2016

(65) Prior Publication Data

US 2016/0210028 A1 Jul. 21, 2016

Related U.S. Application Data

(60) Provisional application No. 62/104,309, filed on Jan. 16, 2015.

(51) Int. Cl.
*G06F 3/0484* (2013.01)
*G06F 3/041* (2006.01)
(Continued)

(52) U.S. Cl.
CPC ..... *G06F 3/04845* (2013.01); *G01R 31/2808* (2013.01); *G03F 7/708* (2013.01);
(Continued)

(58) Field of Classification Search
CPC ......... G06F 2203/04806; G06F 3/0412; G06F 3/04845; G06F 3/04847; G06F 3/04883;
(Continued)

(56) References Cited

U.S. PATENT DOCUMENTS 4,644,172 A * 2/1987 Sandland ......... G01N 21/95607
250/548
5,566,877 A * 10/1996 McCormack ...... G01N 21/8803
228/105
(Continued)

FOREIGN PATENT DOCUMENTS

JP 2000-147070 5/2000
JP 2007-311430 11/2007
(Continued)

*Primary Examiner* — Tadeese Hailu
(74) *Attorney, Agent, or Firm* — McClure, Qualey & Rodack, LLP

(57) ABSTRACT

The instant disclosure provides an operating method of inspecting equipment, with the method applicable to semiconductor inspecting equipment having a movable element. The method includes: displaying a wafer graphic by a touch display; detecting a touch signal generated by the touch display; detecting the magnification of the wafer graphic when the touch signal is generated; and determining the moving speed of the movable element based on the magnification of the wafer graphic when the touch signal is generated. In addition, the moving direction of the movable element can be determined according to the touch signal. Through the instant disclosure, the operator can more intuitively operate each movable element of semiconductor inspecting equipment.

15 Claims, 6 Drawing Sheets

(51) Int. Cl.
  *G06F 3/0488* (2013.01)
  *G01R 31/28* (2006.01)
  *G03F 7/20* (2006.01)
  *G01N 21/95* (2006.01)

(52) U.S. Cl.
  CPC .......... *G03F 7/7065* (2013.01); *G06F 3/0412* (2013.01); *G06F 3/04847* (2013.01); *G06F 3/04883* (2013.01); *G01N 21/9501* (2013.01); *G06F 2203/04806* (2013.01)

(58) Field of Classification Search
  CPC ............. G09G 2310/027; G09G 3/006; G01N 21/9501; G01N 21/8851; G01N 2021/8867; G01N 21/95607; G06T 7/001; G06T 2207/10056; G03F 7/70591; G03F 7/70616
  See application file for complete search history.

(56) References Cited

U.S. PATENT DOCUMENTS

| | | | | |
|---|---|---|---|---|
| 6,084,419 A | * | 7/2000 | Sato | G01R 31/2886 324/750.03 |
| 6,504,948 B1 | * | 1/2003 | Schemmel | G06T 7/001 382/149 |
| 6,987,874 B2 | * | 1/2006 | Hirose | G06T 7/0004 348/126 |
| 8,352,884 B2 | * | 1/2013 | Zalewski | G06F 1/1626 715/811 |
| 8,564,555 B2 | * | 10/2013 | Day | G06F 3/0416 178/18.01 |
| 2003/0059105 A1 | * | 3/2003 | Hirose | G06T 7/0004 382/149 |
| 2003/0080421 A1 | * | 5/2003 | Sawai | H01L 23/3171 257/737 |
| 2003/0173990 A1 | * | 9/2003 | Nanbu | G01N 21/9501 324/754.19 |
| 2003/0231950 A1 | * | 12/2003 | Raaijmakers | H01L 21/681 414/800 |
| 2004/0130727 A1 | * | 7/2004 | Isozaki | G01N 21/9501 356/504 |
| 2006/0265156 A1 | * | 11/2006 | Sun | G01R 31/318511 702/58 |
| 2009/0166557 A1 | * | 7/2009 | Makino | H01J 37/026 250/442.11 |
| 2012/0126118 A1 | * | 5/2012 | Suzuki | H01J 37/026 250/310 |
| 2013/0115030 A1 | * | 5/2013 | Nisany | B65G 47/905 414/225.01 |
| 2013/0252356 A1 | * | 9/2013 | Ezaki | H01L 21/6835 438/18 |

FOREIGN PATENT DOCUMENTS

| | | |
|---|---|---|
| JP | 2014-056192 | 3/2014 |
| TW | M426046 U | 4/2012 |

* cited by examiner

OPERATING METHOD FOR INSPECTING EQUIPMENT

CROSS-REFERENCES TO RELATED APPLICATIONS

This non-provisional application claims priority under 35 U.S.C. § 119(a) on U.S. Provisional Patent Application Ser. No. 62/104,309, filed on 2015 Jan. 16, the entire contents of which are hereby incorporated by reference.

BACKGROUND

Technical Field

The instant disclosure relates to a movement control method of inspecting equipment, in particular to a control method for the movement speed and direction of wafer chuck, image-capturing module, or other movable element.

Related Art

Conventionally, for wafer chucks (or chucks for holding device under test (DUT)), image-capturing module, or probe station of semiconductor inspecting equipment, its movement is solely executed through toggles, mice, buttons, and built-in user operating software of the semiconductor inspecting equipment, with limited user-friendliness and efficiency. However, to date no publications have been found regarding the use of touch signal in controlling the movement of wafer chucks (or chucks for holding DUT), image-capturing module, probe station, and other movable elements.

SUMMARY

Therefore, one of goals of the instant disclosure is to control the movable element of inspecting equipment through a touch signal, in order to move the movable element or inspect device under test (DUT) in a more direct and efficient manner.

One of the principles of the instant disclosure is an operating method of inspecting equipment, applicable to semiconductor inspecting equipment having a movable element. The method comprises: displaying a wafer graphic from a touch display; detecting a touch signal generated by the touch display; detecting the magnification of the wafer graphic when the touch signal is generated; and determining the moving speed of the movable element based on the magnification of the wafer graphic when the touch signal is generated.

DETAILED DESCRIPTION

Figure 1:
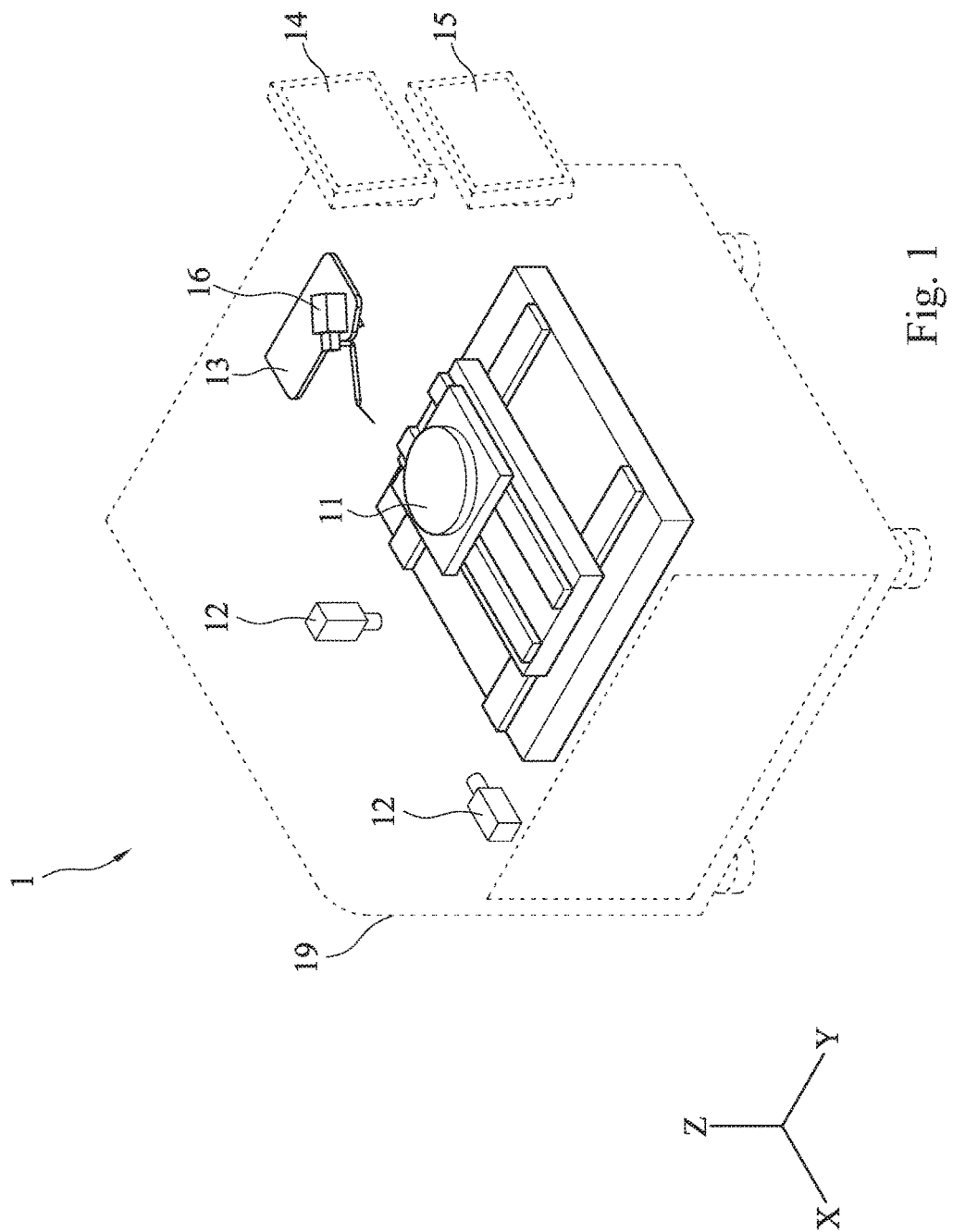
FIG. 1 is a schematic view of semiconductor inspecting equipment.

Please refer to FIGS. 1~4, which are schematic view of semiconductor inspecting equipment and schematic views (first through third) of a wafer graphic, respectively, as examples of illustrating the inspecting equipment and a device under test (DUT). In particular, the first through third schematic views of the wafer graphic show respective wafers under different magnification ratios, with the magnification ratio of the third schematic view of the wafer graphic being greater than that of the second schematic view of the wafer, and the magnification ratio of the second schematic view of the wafer graphic being greater than that of the first schematic view of the wafer. The operating method of inspecting equipment for a first embodiment of the instant disclosure is applicable to semiconductor inspecting equipment 1 having a movable element. As shown in FIG. 1, the semiconductor inspecting equipment 1 comprises a wafer chuck 11, an image-capturing module 12, a probe station 13, a touch display 14, a display 15, a probe base 16, and a body 19. The wafer chuck 11, image-capturing module 12, probe station 13, and probe base 16 are movable elements. The touch display 14 can show wafer graphics, while the display 15 can show images captured by the image-capturing module 12. The probe base 16 is disposed on the probe station 13, with the probe base 16 capable of moving along with the probe station 13 or moving by itself relative to the probe station 13. The image-capturing module 12 may move in a direction along a z-axis above the wafer chuck 11 for image capturing. In addition, the image-capturing module 12 may also move in a direction along an x-axis or y-axis along the sides of the body 19 for image capturing. It should be noted that although the instant embodiment employs related elements and modules of semiconductor inspecting equipment along with wafer graphics for explanation, the instant disclosure is not restricted thereto with other inspecting equipment and DUT graphics also applicable after adjustment. In addition, movable elements are not restricted to the wafer chuck 11, image-capturing module 12, probe station 13, display 15, and probe base 16.

Figure 2:
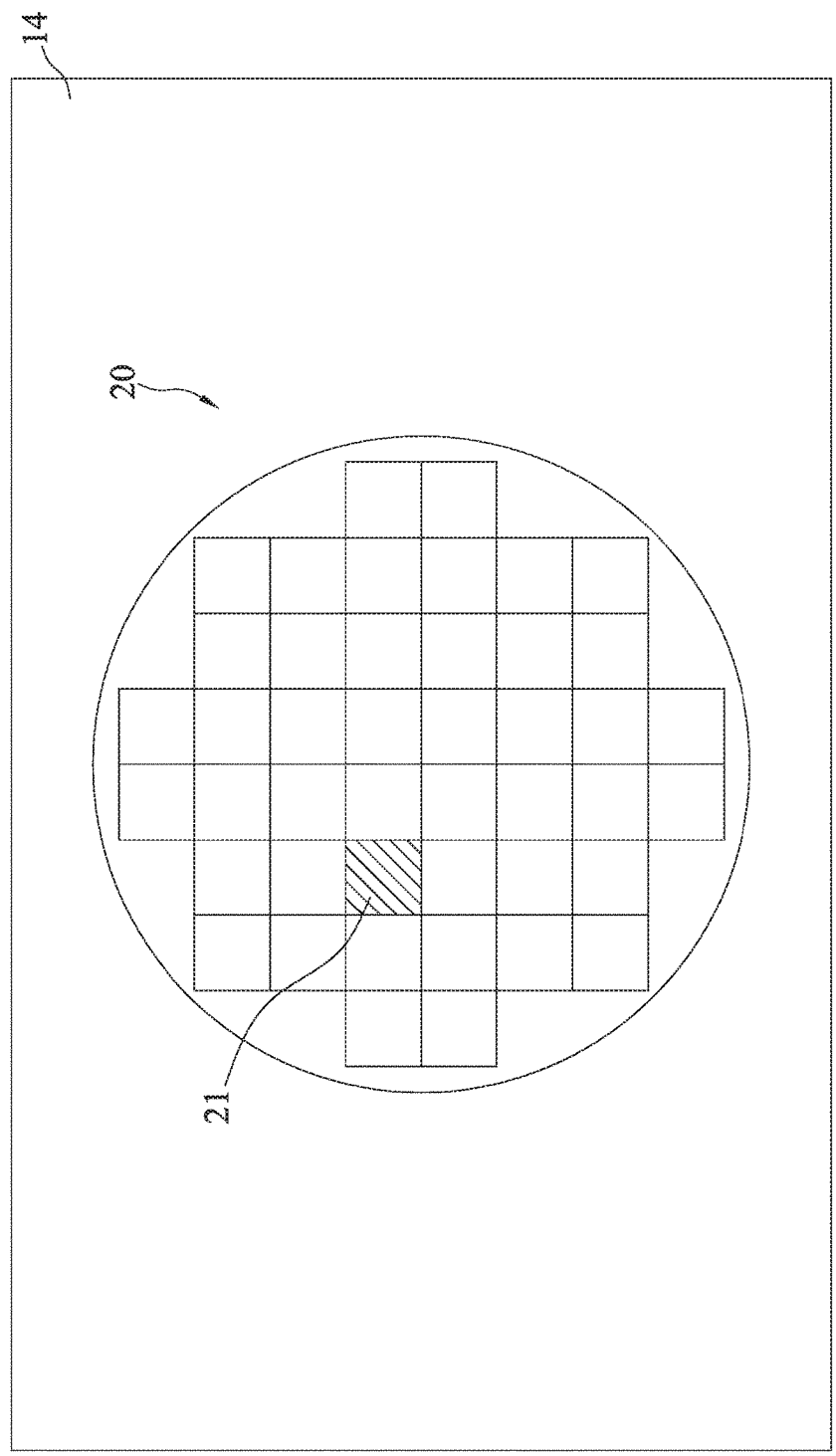
FIG. 2 is a first schematic view of a wafer graphic.
Figure 3:
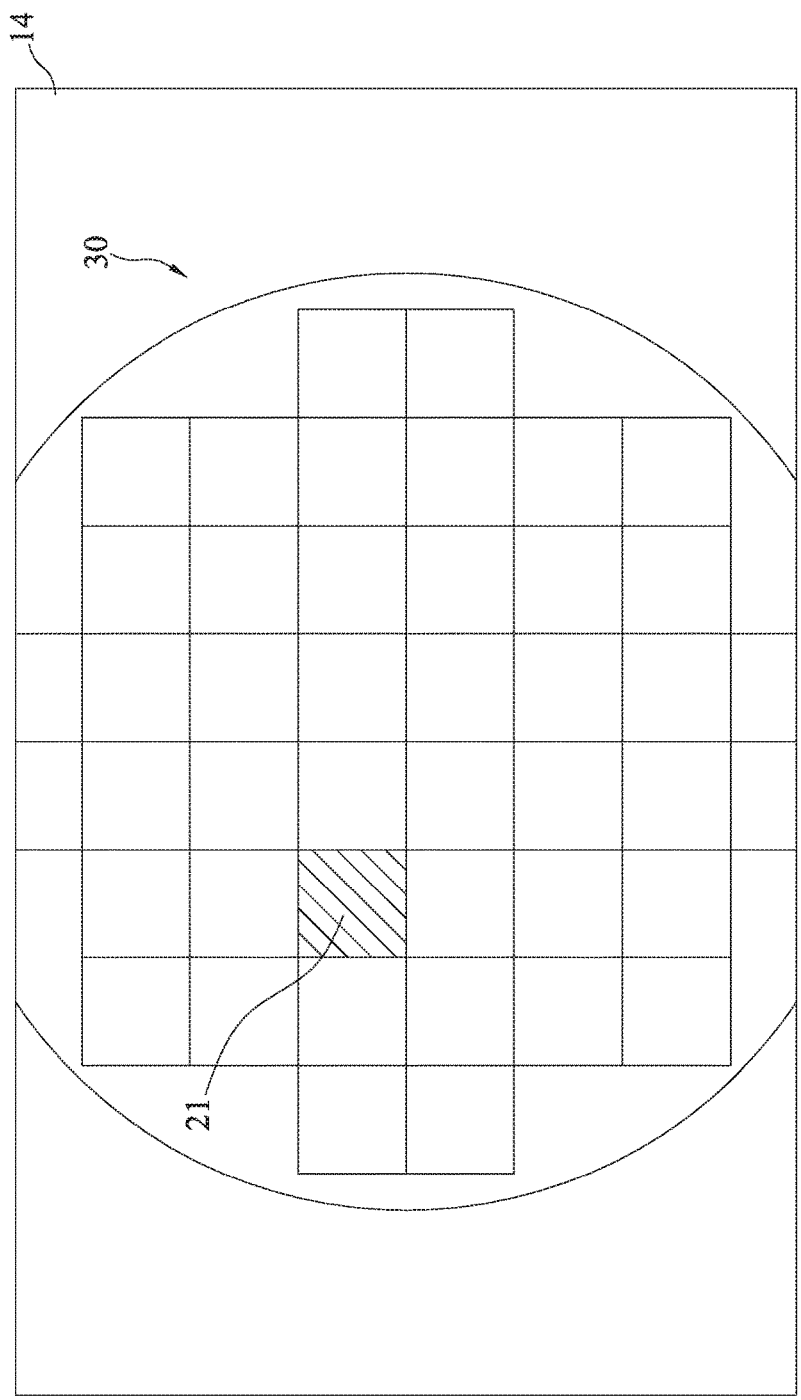
FIG. 3 is a second schematic view of a wafer graphic.
Figure 4:
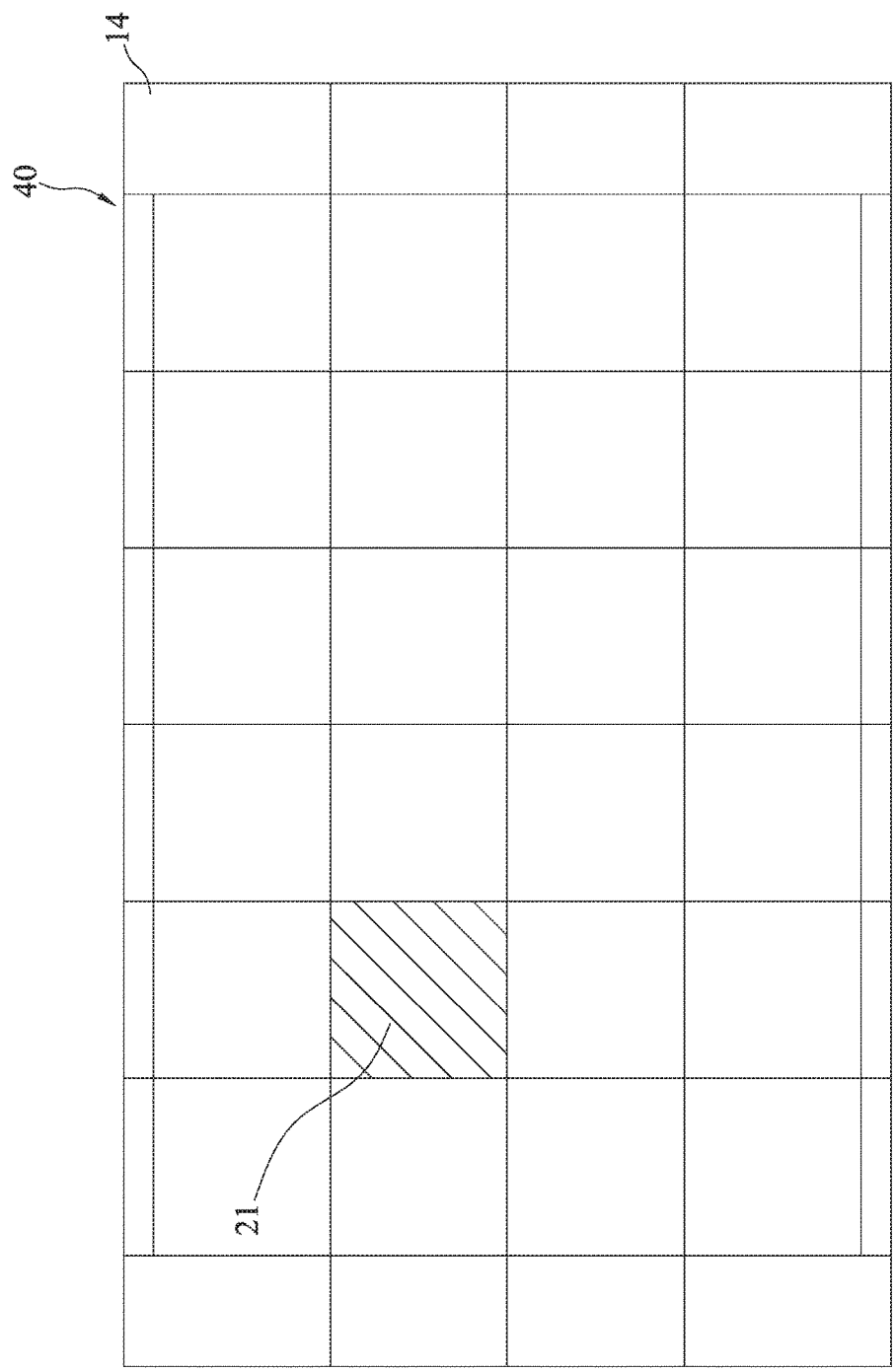
FIG. 4 is a third schematic view of a wafer graphic.

Please refer to FIGS. 2~4. For the first embodiment of the instant disclosure, one of the steps of the operating method of semiconductor inspecting equipment is to display a wafer graphic 20 on the touch display 14. The grids of the wafer graphic 20 represent respective dies of the wafer, with the die labeled by reference numeral 21 being a defective one or the one to be inspected. When the wafer graphic is under a first magnification, as indicated by FIG. 2 with the wafer graphic 20 having a smaller magnification, the image-capturing module 12 has a broader zooming range. That is to say the display 15 shows more dies. When the wafer graphic is under a second magnification, as indicated by FIG. 3 with a wafer graphic 30 having an intermediate magnification, the image-capturing module 12 has a narrower zooming range. That is to say the display 15 shows relatively less dies. When the wafer graphic is under a third magnification, as indicated by FIG. 4 with a wafer graphic 40 having a larger magnification, the image-capturing module 12 has an even narrower zooming range. That is to say the display 15 shows relatively even less dies.

When the magnification is at the first magnification shown by the wafer graphic 20, if an operator uses a finger to slide on the touch display 14, the wafer chuck 11 then moves at a first speed. When the magnification is at the second magnification shown by the wafer graphic 30, if an operator uses a finger to slide on the touch display 14, the wafer chuck 11 then moves at a second speed. When the magnification is at the third magnification shown by the wafer graphic 40, if an operator uses a finger to slide on the touch display 14, the wafer chuck 11 then moves at a third speed. The third speed is less than the second speed, and the second speed is less than the first speed. That is to say the larger the magnification, the slower the wafer chuck 11 moves. Also in other words, when the operator uses a finger to slide for a same distance on the touch display 14, if the wafer graphic is magnified to a greater extent, the corresponding displacement distance of the wafer chuck 11 is smaller. During the displacement operating process of the wafer chuck 11, the image-capturing module 12 continues to capture images of the wafer on the wafer chuck 11. The complete, part, labeling, and/or magnified graphics of the wafer (DUT) are displayed via the display 15 or touch display 14 for monitoring by the operator.

If the touch display 14 has multi-touch capability, the magnification of the aforementioned wafer graphic can be set by the hand gesture of the operator using the touch display 14. For example, when two fingers are moving toward each other on the touch display 14, the wafer graphic shrinks. When two fingers are moving away from each other on the touch display 14, the wafer graphic stretches.

Figure 5:
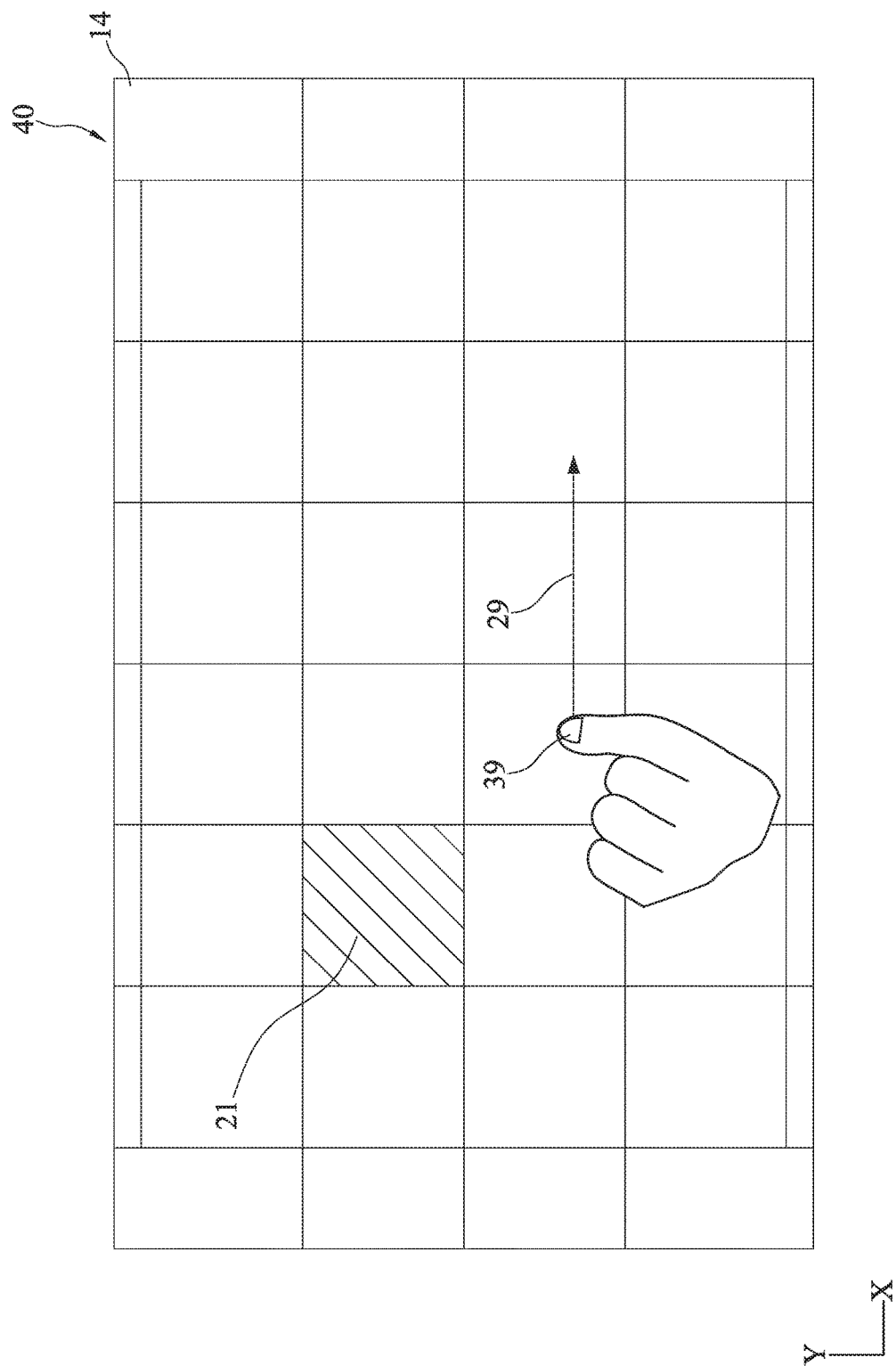
FIG. 5 is a first schematic view of a wafer moving along a finger-sliding direction.
Figure 6:
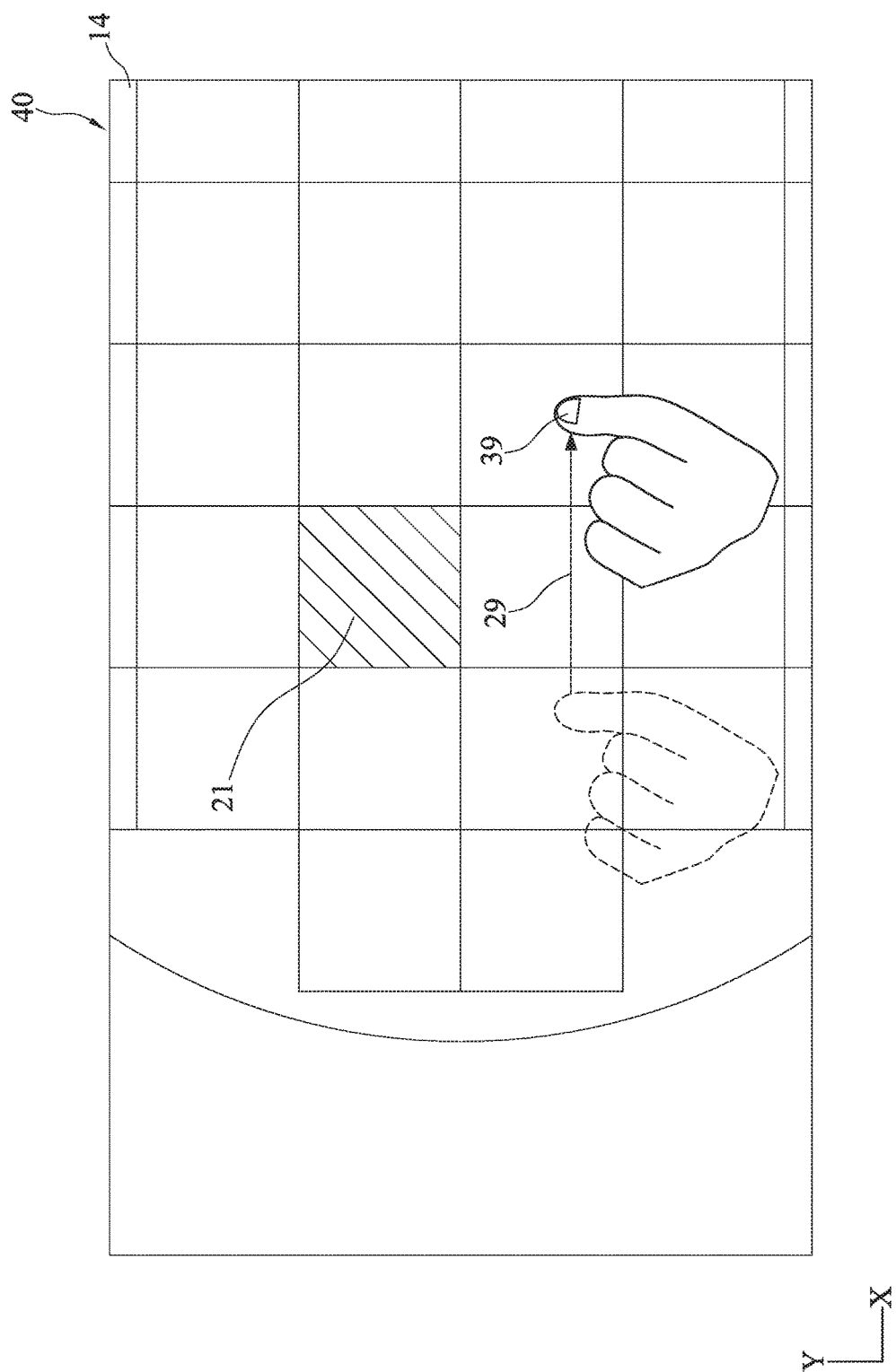
FIG. 6 is a second schematic view of a wafer moving along a finger-sliding direction.

Please refer to FIGS. 5 and 6, which are the first and second schematic views of wafer graphics moving along the finger sliding direction, respectively. For the first embodiment, the touch signal is induced by a slide path 29 on the touch display 14. When the operator slides a finger 39 on the touch display 14 to create the slide path 29, a plurality of touch coordinates corresponding to the slide path 29 are computed in the instant embodiment. The touch coordinates are then used to compute a sliding direction, which is used to determine the moving direction of the movable element (such as the wafer chuck 11, image-capturing module 12, probe station 13, and probe base 16).

In addition, the image of the wafer graphic 40 also moves on the touch display 40 according to the sliding direction of the finger 39. The movement speed and direction of the wafer graphic 40 depends on the sliding speed and direction of the finger 39. When the finger 39 slides on the touch display 14, the wafer graphic 40 slides in real time accordingly.

Based on the above, a sliding speed can also be computed according to computed touch coordinates in the instant embodiment. The moving speed of the movable element is then determined based on the computed sliding speed. For example, a comparison table between the sliding speed and moving speed can be built in the semiconductor inspecting equipment 1. When the computed sliding speed is greater than or equal to a first value and less than a second value, the moving speed is V1. When the computed sliding speed is greater than or equal to the second value and less than a third value, the moving speed is V2, and so forth. In other words, the moving speed of the movable element can be determined via the comparison table, not necessarily by a particular algorithm for computing and determining the moving speed of the movable element. In the above, if the third value is greater than the second value and the second value is greater than the first value, then V2 is greater than V1.

Thus, the first embodiment utilizes the magnification of the wafer graphic shown on the touch display 14 to determine the moving speed of the movable element. As the magnification of the wafer graphic increases, the moving speed of the wafer chuck 11 decreases. The reason being as the wafer graphic is magnified, the zooming range of the image-capturing module 12 is narrowed. At this condition, if the wafer graphic is moved too quickly, the target die for observation is likely to be outside of the image-capturing range. In addition, the first embodiment can also utilize the sliding direction of the finger of the operator on the touch display 14 to determine the moving direction of the movable element. Based on the instant embodiment, the control of each movable element of the semiconductor inspecting equipment 1 becomes more intuitive, and the operations of these elements are more user-friendly.

A second embodiment of the instant disclosure is also for an operating method of inspecting equipment, with this method applicable to the semiconductor inspecting equipment 1 having movable elements. The movable element is selected among the wafer chuck 11, image-capturing module 12, probe station 13, and the probe base 16. The instant embodiment also features displaying a wafer graphic from the touch display 14, along with computing touch coordinates corresponding to the slide path 29 induced by the finger 39 of the operator on the touch display 14. Then, the sliding direction is computed based on the computed touch coordinates, before determining the moving direction of the movable element based on the computed sliding direction.

The second embodiment also can further detect the magnification of the wafer graphic when the touch signal is generated. Based on the magnification of the wafer graphic when the touch signal is generated, the moving speed of the movable element is then determined. When the touch signal is generated, the larger the magnification of the wafer graphic, the lower the moving speed of the movable element. Likewise, the second embodiment also can further compute the sliding speed and direction according to the touch coordinates, followed by determining the moving speed and direction of the movable element based on the computed sliding speed and direction of the finger 39. In addition, based on the computed sliding direction of the finger 39, the wafer graphic 40 may move accordingly in real time on the touch display 14.

For the instant embodiment, the wafer chuck 11 is illustrated to move along the xy plane but is not restricted thereto, while the image-capturing module 12, probe station 13, and probe base 16 can further move along the z axis, or in other words being able to rise or fall relative to the wafer chuck 11. To allow the operator having control of lifting and lowering the image-capturing module 12, the probe station 13, and the probe base 16 via the touch display 14, the touch display 14 may be furnished with a real or virtual on/off switch. Thus, when the operator uses the finger to move up and down on the touch display 14, the operator can determine to control the movable element moving along the y or z axis. In addition, the on/off switch or operation control switch of the movable element can be disposed at other locations, such as a control console (not shown) but is not restricted thereto.

The wafer graphics in the abovementioned embodiments may be figures converted from processed data, image files based on actual images obtained by the image-capturing module 12, or other forms of representative figures.

The instant disclosure also provides an operating method of inspecting equipment, where the method is applicable to semiconductor inspecting equipment having a movable element. The movable element may be selected among the wafer chuck, image-capturing module, probe station, and probe base. The method comprises:

S110: Displaying a wafer graphic by a touch display;

S120: Detecting a touch signal generated by the touch display;

S130: Detecting the magnification of the wafer graphic when the touch signal is generated; and S140: Determining the moving speed of the movable element based on the magnification of the wafer graphic when the touch signal is generated.

The instant disclosure provides another operating method of inspecting equipment, where the method is applicable to semiconductor inspecting equipment having a movable element. The movable element may be selected among the wafer chuck, image-capturing module, probe station, and probe base. The method comprises:

S210: Displaying a wafer graphic by a touch display;

S220: Detecting a touch signal generated by the touch display, where the touch signal is induced by a slide path shown on the touch display;

S230: Computing the touch coordinates corresponding to the slide path;

S240: Computing the sliding direction according to the touch coordinates;

S250: Determining the moving direction of the movable element based on the sliding direction.

The instant disclosure further provides another operating method of inspecting equipment, where the method is applicable to inspecting equipment having a movable element. The movable element may be selected among the DUT chuck and image-capturing module. The method comprises:

S410: Displaying a DUT graphic by the touch display;

S420: Detecting a touch signal generated by the touch display;

S430: Detecting the magnification of the DUT graphic when the touch signal is generated; and S440: Determining the moving speed of the movable element based on the magnification of the DUT graphic when the touch signal is generated.

Details of the above-provided embodiments of the operating method can be obtained from the above-described description, and are not elaborated here for conciseness.

Based on the above disclosed description, the instant disclosure provides control of the movable element of inspecting equipment via the touch signal, such that the movable element can be moved or the DUT can be inspected in a more direct and efficient manner.

While the instant disclosure has been described by way of example and in terms of the preferred embodiments, it is to be understood that the instant disclosure needs not be limited to the disclosed embodiments. For anyone skilled in the art, various modifications and improvements within the spirit of the instant disclosure are covered under the scope of the instant disclosure. The covered scope of the instant disclosure is based on the appended claims.

What is claimed is:

1. An operating method of inspecting equipment, applicable to semiconductor inspecting equipment having a movable element, with the movable element selected among a wafer chuck, an image-capturing module, a probe station, and a probe base, comprising:
   displaying a wafer graphic by a touch display;
   detecting a touch signal generated by the touch display;
   detecting the magnification of the wafer graphic when the touch signal is generated; and
   determining the moving speed of the movable element based on the magnification of the wafer graphic when the touch signal is generated.

2. The method of claim 1, wherein the larger the magnification of the wafer graphic when the touch signal is generated, the lower the moving speed of the movable element.

3. The method of claim 1, wherein the touch signal is induced by a slide path shown by the touch display and the method further comprises:
   computing the touch coordinates corresponding to the slide path;
   computing the sliding direction according to the touch coordinates; and
   determining the moving direction of the movable element based on the sliding direction.

4. The method of claim 3, further comprising:
   moving the wafer graphic in real time shown on the touch display according to the sliding direction.

5. The method of claim 3, further comprising:
   computing a sliding speed based on the touch coordinates; and
   determining the moving speed of the movable element according to the sliding speed.

6. The method of claim 5, further comprising:
   moving the wafer graphic in real time shown on the touch display according to the sliding speed.

7. An operating method of inspecting equipment, applicable to semiconductor inspecting equipment having a movable element, with the movable element selected among a wafer chuck, an image-capturing module, a probe station, and a probe base, comprising:
   displaying a wafer graphic by a touch display;
   detecting a touch signal generated by the touch display, wherein the touch signal is induced by a slide path shown on the touch display;
   computing the touch coordinates corresponding to the slide path;
   computing the sliding direction according to the touch coordinates;
   determining the moving direction of the movable element based on the sliding direction.

8. The method of claim 7, further comprising:
   detecting the magnification of the wafer graphic when the touch signal is generated; and
   determining the moving speed of the movable element based on the magnification of the wafer graphic when the touch signal is generated;
   wherein the larger the magnification of the wafer graphic when the touch signal is generated, the lower the moving speed of the movable element.

9. The method of claim 7, further comprising:
   computing a sliding speed based on the touch coordinates; and
   determining the moving speed of the movable element according to the sliding speed.

10. The method of claim 9, further comprising:
    moving the wafer graphic in real time shown on the touch display according to the sliding speed.

11. The method of claim 7, further comprising:
    moving the wafer graphic in real time shown on the touch display according to the sliding direction.

12. The method of claim 7, wherein the movable element is the wafer chuck and the method further comprises:
    determining a moving direction of the wafer chuck along a plane according to the sliding direction.

13. The method of claim 7, wherein the movable element is selected among the image-capturing module, probe station, and probe base and the method further comprises:
    determining whether the movable element is moving upward or downward according to the sliding direction.

14. An operating method of inspecting equipment, applicable to inspecting equipment having a movable element, with the movable element selected among a device under test (DUT) chuck and an image-capturing module, comprising:
    displaying a DUT graphic by a touch display;
    detecting a touch signal generated by the touch display;
    detecting the magnification of the DUT graphic when the touch signal is generated; and determining the moving speed of the movable element based on the magnification of the DUT graphic when the touch signal is generated.

15. The method of claim 14, wherein the larger the magnification of the DUT graphic when the touch signal is generated, the lower the moving speed of the movable element.

* * * * *